United States Patent [19]

Sengupta

[11] Patent Number: 5,155,209

[45] Date of Patent: * Oct. 13, 1992

[54] R-(+) ENANTIOMERIC FORM OF 7-(2, 3-EPOXYPROPOXY) ACTINOMYCIN D

[75] Inventor: Sisir Sengupta, Needham, Mass.

[73] Assignee: Trustees of Boston University, Boston, Mass.

[*] Notice: The portion of the term of this patent subsequent to Apr. 30, 2002 has been disclaimed.

[21] Appl. No.: 747,893

[22] Filed: Aug. 19, 1991

Related U.S. Application Data

[63] Continuation of Ser. No. 256,024, Oct. 11, 1988, abandoned.

[51] Int. Cl.$^5$ .............. A61K 37/02; C07K 5/00; C07K 7/00; C07K 15/00
[52] U.S. Cl. ............................. 530/317; 530/330
[58] Field of Search ................ 530/317, 330; 514/17

[56] References Cited

U.S. PATENT DOCUMENTS 4,514,330  4/1985  Sengupta et al. ................ 530/317

OTHER PUBLICATIONS

Sengupta et al, J. Med. Chem. vol. 31, (1988), pp. 1540-1547.
Sengupta et al, J. Med. Chem., vol. 27, (1984), pp. 1465-1470.
Sengupta et al, J. Med. Chem. vol. 25, (1982), pp. 1214-1219.
Zbaida et al., Chemical Abstracts, 1988, CA108:94941f.
March, "Advanced Organic Chemistry", N.Y.: McGraw Hill Bk. Co. 1977, pp. 106-111.
Karrer, "Organic Chemistry" (Second English Ed.) N.Y., 1946, pp. 94-97.
Shafer et al., Biochemistry, vol. 21, 1982, pp. 6496-6503.
Barry, III, et al., Biochemistry, vol. 28, 1989, pp. 6323-6333.
Jeannesson et al., Cancer Research, vol. 50, Feb. 15, 1990, pp. 1231-1236.

*Primary Examiner*—Lester L. Lee
*Assistant Examiner*—Avis Davenport
*Attorney, Agent, or Firm*—Paul J. Cook; Lawrence Gilbert

[57] ABSTRACT

The R-(+) enantiomeric form of ± racemic 7-(2, 3-empoxypropoxy) actinomycin D (EPA) is provided which is effective in the therapeutic treatment of cancer. The analogue has the formula:

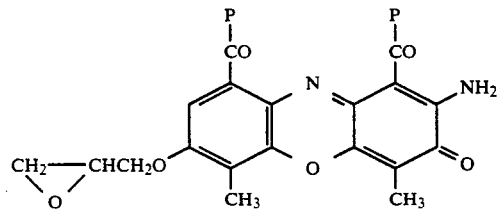

wherein the P's are:

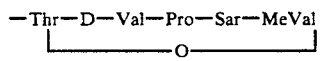

The enantiomeric form is uniformly superior to other forms of the compound in treating malignant tumors.

1 Claim, No Drawings

R-(+) ENANTIOMERIC FORM OF 7-(2, 3-EPOXYPROPOXY) ACTINOMYCIN D

This is a continuation of co-pending application Ser. No. 07/256,024 filed on Oct. 11, 1988 and now abandoned.

BACKGROUND OF THE INVENTION

This invention relates to a new analogue of actinomycin D and to a method of preparing it.

Actinomycin D (AMD) is disclosed in German Patent No. 1,172,680 and is a chromopeptide antibiotic whose potent activity in several tumors, including Wilm's tumor, gestational choriocarcinoma and Kaposi's sarcoma, has been reported. It has the formula:

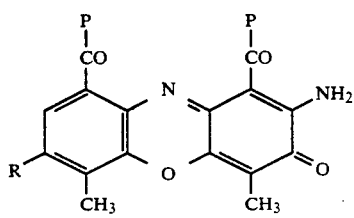

wherein the Ps are:

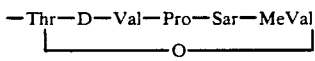

and R is hydrogen. AMD at submicromolar concentrations strongly inhibits DNA-dependent RNA synthesis and, to a lesser extent, DNA synthesis. Its interaction with DNA has been extensively studies, and the details of the mechanism of binding to DNA has been proposed, E. Reich, Cancer Res., 23,1428 (1963), W. Muller and D. M. Crothers, J. Mol. Biol., 35,251 (1968), and H. M. Sobell and S. C. Jain, J. Mol. Biol., 68, 21 (1972). It has been assumed that the cytoxicity of AMD is due to its inhibition of RNA polymerase following the intercalative binding to DNA. It is quite possible, however, that the distortions in helical DNA resulting from the strong noncovalent association with AMD may not be solely responsible for the observed biological effects. For example, Nakazawa et al, J. Org. Chem., 46, 1493 (1981) suggest that an intermediate free-radical form of AMD may be the active form that causes DNA damage and cell death.

Furthermore, the proximal mechanism of biochemical action of AMD, which is evident from the inhibition of RNA synthesis, may not be the principal mechanism of selective cytoxicity of the agent at the pharmacological level. For it is known that AMD is far more cytotoxic in those proliferating cells in which it inhibits DNA synthesis than in those of liver, kidney, muscle, etc., that are nonproliferating but are heavily dependent upon RNA synthesis for protein renewal.

Another pharmacological behavior of AMD is that it is not metabolized in vivo. Absence of metabolic conversion or detoxification of AMD leads to its accumulation in the cell nuclei of the host organs which causes cumulative toxicity. This acute cumulative toxicity limits the wide clinical application of AMD.

Reverse analogues and a symmetrical analogue of AMD useful in treating cancer are disclosed in U.S. Pat. No. 4,680,382.

Accordingly, it would be desirable to synthesize and isolate new pharmacologically active analogues of AMD having increased drug efficacy. To achieve this, it would be desirable to increase the drug potency, by enhancing drug activity in the tumor cells, decrease toxicity to the host and improve means for administering the drug.

SUMMARY OF THE INVENTION

In describing this invention, the following notations as relates to the products of this invention is shown by Formula 3b.

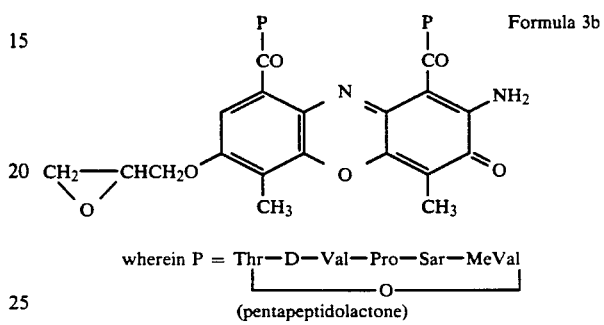

The compound in its pure form is novel and is active and toxic against human cancer cells.

The compound of this invention as well as closely related compounds to be tested for anticancer activity are produced by the schematic process as shown in Chart I.

DESCRIPTION OF SPECIFIC EMBODIMENTS

Some chemical and biological properties of racemic 7-(2,3-epoxypropoxy) actinomycin D[($\pm$)-EPA, ($\pm$)-3b] are disclosed in J. J. Med. Chem., 1982, Vol. 21, Pg. 1214 and J. J. Med. Chem., 1984, Vol. 27, pag. 1465. This analogue was synthesized by substituting at carbon-7 of the chromophore in actinomycin D (AMD, 1b) with an alkylating function that rendered this analogue a novel dual action DNA-binding agent, i.e., binding to DNA by both intercalation and alkylation. This analogue binds exclusively to guanine bases in DNA and demonstrates high antitumor activity in human lymphoblastic leukemia (CCRF-CEM) cells in vitro, and P388/S mouse leukemia in vivo.

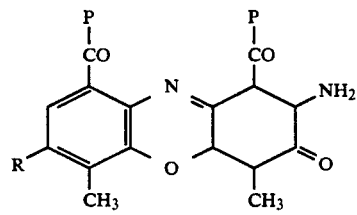

a. P = N(CH$_3$)$_2$ b. 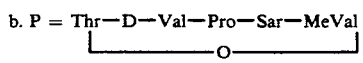

1. R = H (AMD: 1b)

2. R = OH(7-hydroxy-AMD:2b)

3. R = OCH$_2$CH—CH$_2$ (EPA: 3b)
      \\    /
        O

4. R = OCH₂CH—CO₂CH₃
       |
       OH

5. R = OCH₂CH—CH₂  (DHPA: 5b)
       |    |
       OH   OH

6. R = OCH₂CH—CH₂
       |    |
       OH   O-pTs

7. R = OCH₂CH—CH₂—O-MPTA
       |
       O-MPTA

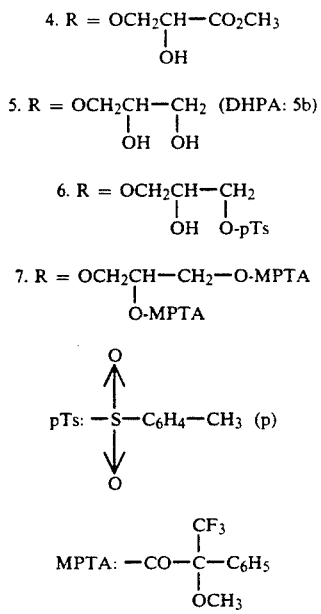

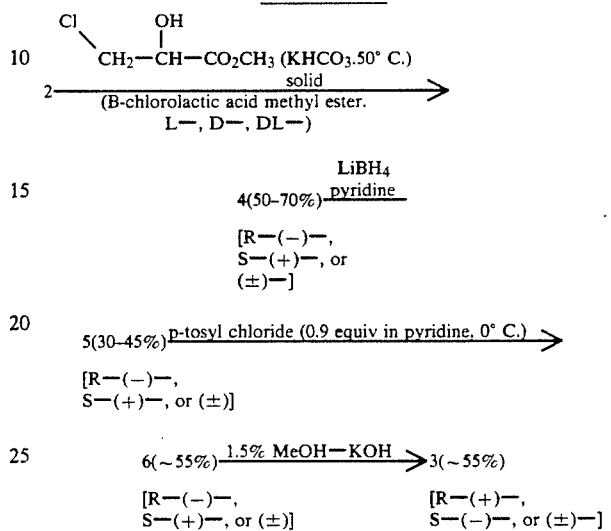

It has been found, in accordance with this invention that the R-(+) form of EPA is superior to other entantiomeric forms of EPA in treating malignant tumors. The R-(+) form of EPA is isolated by the procedure set forth below while significant yields of the entantiomer are not achieved with conventional resolution on a chiral HPLC column or by conventional asymmetric epoxidation of an intermediate olefin.

Chemical studies are done with model analogues in which the peptide lactone rings are replaced with two dimethylamine functions. The chemical and ultraviolet spectral natures of these model analogues (1a–7a) are very similar to the respective actinomycin analogues (1b–7b, Chart I), but their use offers several advantages; they are relatively easy to prepare in large quantities and the chemical reactions made on them can be applied to the actinomycin chromophore directly without major modifications. Also, their H NMR spectra are relatively simple, and since 2a has no methylene proton peaks, the characterization of enantiomeric methine and methylene protons in the epoxy and dihydroxypropoxy groups in 3a and 5a can be easily made. Further, the starting model analogues 1a and 2a themselves do not have a center of asymmetry, and therefore, it is easy to characterize the optical antipodes of 3a and 5a on the basis of acquired D-(+)- or L-(−) rotatoary properties. On the other hand, actinomycin and analogues have ten optically active amino acids in their two peptide lactone rings (P). Proton NMR spectra of actinomycin D (AMD) is relatively complex.

Compound 1a is an old compound and is converted to 7-hydroxy model compound 2a by the procedure described in J. J. Med. Chem, 1975, Vol. 18, pg 1175. The latter was used as the starting material for the synthesis of the intermediate enantiomers 4a and 6a leading to the desired enantiomeric forms of 5a and 3a, respectively (Chart I).

A sequential chemical procedure for the synthesis of R-(+) and S-(−) antipodes of (±)-EPA in high enantiomeric purity utilized in the present invention since attempts to generate the desired enantiomerically enriched forms either via resolution on a chiral HPLC column or by asymmetric epioxidation of an intermediate olefin were unsuccessful. The synthesis of the enantiomers of analogues 3–7 in relatively pure forms (>90%) (Chart I) is carried out following the sequence of reactions shown in Scheme I.

DL-, D-, or L-halo lactic acid methyl esters are condensed with 7-hydroxy analogues 2 (a or b) by using solid potassium bicarbonate in a heterogeneous-phase reaction yielding the enantiomers of 7-(2-hydroxy-2-carbomethoxyethoxy) chain substituted compounds (4) in 97% purity and in good to moderate yields, depending on the starting (2a or 2b) compound and the halo ester employed (see Example). These products are converted to the 7-(2,3-dihydroxypropoxy) chain substituted analogues (5) by a LiBH₄ in pyridine mediated reduction of the carbomethoxy group. The enantiomeric forms of 5 are obtained in 95% purity and in 30–45% yield. The resulting dihydroxy chain substituted compounds are selectively tosylated to 7-(2-hydroxy-3-tosyl) oxy group substituted analogues (6) reacting with a subequimolar [(0.9 molar ratio of p-toluenesulfonyl (p-tosyl)chloride] in order to tosylate only the primary 3-hydroxyl function and to prevent reaction of the secondary 2-hydroxyl function, which might lead to decreased enantiomeric purity of the products. The progress of the reaction is monitored by HPLC and NMR and the products are identified by their physiochemical characteristics, including elemental and mass spectometric analysis. The tosyl derivatives in enantiomeric purity of 90% are isolated in moderate yields, and these are cyclized to oxirane (epoxy) rings by the trans side elimination of the monotosyl function by reaction with 1.5% methanolic KOH at ambient temperature. Thus, the R-(−) enantiomer of (6) produces the R-(+) enantiomer of (3). The reaction is monitored by TLC for actinomycin analogue (6b), insuring that no rupture of the peptide lactone rings occurs during the course of this reaction in methanolic KOH. The final products in enantiomeric forms are isolated in yields of about 55% without any appreciable racemization and in enantiomeric excess of 80% (90% purity). The physiochemical data are set forth in Tables I and II.

TABLE I

Physical Properties of Carbon-7-Substituted Model Analogues of Actinomycin D

| compd | R | ep | mol formula |
|---|---|---|---|
| 1a | H | | $C_{20}H_{22}N_4O_4$ |
| 2a | OH | | $C_{20}H_{22}N_4O_5$ |
| 3a | 2,3-epoxypropoxy group | 0 | $C_{23}H_{26}N_4O_6$ |
| | R-(+)enantiomer | 90 | |
| | S-(−)enantiomer | 90 | |
| 4a | $OCH_2CH(OH)COOCH_3$ | 0 | $C_{24}H_{28}N_4O_8$ |
| | R-(−)enantiomer | 97 | |
| | S-(+)enantiomer | 97 | |
| 5a | $OCH_2CH(OH)CH_2OH$ | 0 | $C_{23}H_{26}N_4O_7$ |
| | R-(−)enantiomer | 95 | |
| | S-(+)enantiomer | 95 | |
| 6a | $OCH_2CH(OH)CH_2OTS$ | 0 | $C_{30}H_{34}N_4O_9S$ |
| | R-(−)enantiomer | 90 | |
| | S-(+)enantiomer | 90 | |
| 7a | $OCH_2CH(OR-(+)-$ MTPA) $CH_2OR-(+)$-MTPA | | $C_{43}H_{42}N_4O_{11}F_6$ |
| | R-(+),R-(−)enantiomer | 95 | |
| | R-(+),S-(+)enantiomer | 95 | |

| Comp. | $t_R,^b$ min | $[\alpha]^{20}_D$ deg $[c,CHCl_3]^c$ | $^1$H NMR signal for R, $\alpha^b(\alpha)$ values in brackets are for CH(OH) proton only |
|---|---|---|---|
| 1a | 11.8 | ±0 | 7.33 (s,1H) |
| 2a | 15.6 | ±0 | 6.80 (s,1H) |
| 3a | 23.5,21.1 | ±0 | 3.7(d,2H),4.12(m,1H) |
| | 23.5 | +8.8(5.1) | [3.98(m,1H)] |
| | 20.9 | −8.8(5.0) | [3.98(m,1H)] |
| 4a | 34.0,36.8 | ±0 | 2.85(s,3H,CH₃),4.56(t,1H), 3.36(d,2H),6.90(d,1H), (peak at 6.90,D₂O exchangeable) |
| | 34.0 | −4.8(11.0) | [4.44(t,1H)] |
| | 37.0 | +4.7(11.3) | [4.68(t,1H)] |
| 5a | 30.1,28.0 | ±0 | 3.75(d,2H),4.2–4.35(1H),3.20 (d,2H),6.92(br,1H),7.1 (br,1H) |
| | 30.9 | −6.8(7.7) | [4.24(dd,1H)] |
| | 28.5 | +6.1(7.5) | [4.33(dd,1H)] |
| 6a | 20.8,22.7 | ±0 | 2.42(s,3H),4.15(dd,4H),6.88 (1H),4.95(m,1H),7.43(2H),7.7 (d,2H) |
| | 20.5 | −7.8(4.6) | [4.90 (m,1H)] |
| | 22.7 | +7.5(4.4) | [4.99 (m,1H)] |
| 7a | 6.6,9.9 | ±0 | 5.18(q,3F),4.91(q,3F). 4.70–4.00(overlapping 6F) |
| | 6.1 | −54.0(1.0) | 5.22(q,3F),4.74(q,3F) |
| | 9.8 | +50.9(1.2) | 4.90(q,3F),4 09(q,3F) |

TABLE II

Physiochemical Properties Carbon-7-Substituted Analogues of Actinomycin

| compd | R | $ep^a\%$ | mol formula |
|---|---|---|---|
| 1b | H | | $C_{62}H_{862}N_{12}O_{16} \cdot 2H_2O$ |
| 2b | OH | | $C_{62}H_{88}N_{12}O_{17} \cdot H_2O$ |
| 3b | 2,3-epoxypropoxy group | 0 | $C_{65}H_{90}N_{12}O_{18} \cdot 2H_2O$ |
| | R-(+)enantiomer | 90 | |
| | S-(−)enantiomer | 90 | |
| 4b | $OCH_2CH(OH)COOCH_3$ | 0 | $C_{66}H_{92}N_{12}O_{20} \cdot 2H_2O$ |
| | R-(−)enantiomer | 97 | |
| | S-(+)enantiomer | 97 | |
| 5b | $OCH_2CH(OH)CH_2OH$ | 0 | $C_{65}H_{92}N_{12}O_{19} \cdot 2H_2O$ |
| | R-(−)enantiomer | 95 | |
| | S-(+)enantiomer | 95 | |
| 6b | $OCH_2CH(OH)CH_2OTS$ | 0 | $C_{72}H_{98}N_{12}O_{21}S$ |
| | R-(−)enantiomer | 90 | |
| | S-(+)enantiomer | 90 | |
| 7b | $OCH_2CH(OR-(+)-$MTPA)$CH_2OR-(+)$-MTPA | | $C_{85}H_{106}N_{12}O_{23}F_6 \cdot H_2O$ |
| | R-(+),R-(−)enantiomer | 95 | |
| | R-(+),S-(+)enantiomer | 95 | |

| Comp. | $t_R,^b$min | $[\alpha]^{20}_D$deg $[c,CHCl_3]^c$ | H NMR signal for 2-CH—OH (R) proton only, $\alpha^b$ |
|---|---|---|---|
| 1b | 16.9 | −360 ±22(0.15) | 7.53 |
| 2b | 19.0 | −298 ±20(0.15) | 8.11 |
| 3b | 30.0,26.7 | −400 ±25(0.15) | 3.98–4.11(m,1H) |
| | 30.1 | −380 +20(0.15) | 3.99(m,1H) |
| | 26.5 | −408 ±18(0.15) | 4.21(m,1H) |
| 4b | 46.7,43.3 | −201 ±15(0.15) | 4.55–4.88(t,1H), |
| | 46.7 | −207 ±15(0.15) | 4.50(t,1H) |
| | 43.0 | −200 ±15(0.15) | 4.77(t,1H) |
| 5b | 40.5,36.7 | −308 ±15(0.15) | 4.33–4.50(m,1H) |
| | 40.0 | −322 ±15(0.12) | 4.35(m,1H) |
| | 36.0 | −299 ±15(0.15) | 4.45(m,1H) |
| 6b | 27.8,21.8 | −101 ±12(0.20) | 4.97–5.11(m,1H) |
| | 28.0 | −103 ±10(0.30) | 4.90(M,1H) |
| | 21.2 | −98 ±11(0.30) | 5.10(m,1H) |
| 7b | 7.7,5.7 | −253 ±30(0.30) | 5.22–4.48(m,12F) |
| | 8.0 | −230 ±30(0.30) | 5.28(q,3F),4.80(q,3F) |
| | 5.0 | −238 ±30(0.30) | 4.97(q,3F),4.45(q,3F) |

[a]Enantiomeric purity (percent) indicates percent population of the major enantiomer.
[b]Retention time in HPLC in minutes, with a Varian MCH-10C₁₈ column and a pH 7 Trisphosphate buffer solution containing 2.5% methanol as an eluant.
[c]Concentration denoted by c in grams/100 milliliters.
[d]Proton NMR spectra were obtained on a JEOL FQ 90-90 MHz or 300-MHz Varian XI spectrometer with deutriochloroform as solvent and approximately 2% tetramethyl silane as an internal standard.
[e]The fluorine NMR spectra were determined with a Varian HA-100 (94.1 MHZ) spectrometer with a solvent mixture of 80% of deuteriochloroform and approximately 20% trifluoroacetic acid by volume as an internal standard added immediately prior to the determination; alternatively, it was used as an external standard when the investigations were to be carried for a prolonged period to avoid any destructive reaction of this acid on samples.

Attempts were made to resolve the racemic mixtures of (±) EPA by chromatography on chiral HPLC columns. With use of Pirkle 1-A column packed with (R)-N-[(3,5-dinitrobenzoyl)phenyl]glycine ionically bonded to aminopropyl siliconized silica (Experimental Section) and with use of 20% MeOH-20-mM NH₄OAc, pH 6.6 as eluant. The components could be enriched and the enriched R-(+) component, tested in vitro against CCRF-CEM and L1210 leukemia cell lines, demonstrated superior activities compared to either the racemic and S-(−) enriched mixtures. Estimation of the enantiomeric percentage in each mixture is made by the resolution of the methine peaks with NMR chiral shift agent Eu(hfc)₃, and integration of the peak areas. All attempts to resolve these mixtures any further failed, probably because of the formation of formidable eutectics that are not resolvable by simple HPLC procedures. Next, a single-step asymmetric epoxidation to the desired enantiomers was attempted. With 7-(allyloxy) actinomycin D as the starting material, oxirane ring formation is attempted with the use of a chiral catalyst FeT (α, β, α, β, Binap) PPCl and iodosylmesitylene as an oxidant. In this procedure, the asymmetry is induced selectively by a transfer of an oxygen atom from the iodosyl group through the intermediacy of the oxidized iron-porphyrin catalyst. The stereochemistry of the epoxy product is conferred by the conformational mobility of the chiral appendages and the nonbonded interaction between the catalyst and the substrate surfaces. The procedure is complex, and the isolation of products requires extensive purification with TLC, which again gave another mixture of components; however, the R-(+) isomer is obtained in an enantiomeric ratio of 7:3 in good yield (69%), and this mixture shows further promising activity in vitro HT-29 human colon carcinoma and in vivo L1210 leukemia. Thus, even these partially enriched enantiomeric forms provide important information about the R-(+) enantiomer as the primary active component of (±)-EPA.

The biochemical and the biological studies described below are done by using the aforementioned 90% enantiomeric purity (90:10) of (R)-(+)-EPA and (S)-(−)-EPA; the properties and the activities of the enantiomers are reported in Tables III-V.

TABLE III

Covalent and Noncovalent (Intercalative) Binding to Calf Thymus DNA. Antitumor Activity (in Vitro and in Vivo) against Actinomycin Resistant (P388/ADR) and in Vitro Activity in Sensitive (B16) Cells by Actinomycin Analogues

| compd | $Tm^a$ | [DNA base]/[drug] $A^b$ | $B^c$ | inhibition of growth $ID^d_{50}nM$ P388/ADR | B16 |
|---|---|---|---|---|---|
| 1b(AMD) | 7.1 ± 0.15 | 26 ± 2 | ND | 2500 ± 250 | 3.0 ± 1.0 |
| 3b[(±)-EPA] | 5.2 ± 0.95 | 32 ± 1 | 480 ± 10 | 80 ± 11 | 2.5 ± 0.6 |
| (R)-(+)-EPA | 4.8 ± 1.15 | 30 ± 2 | 500 ± 15 | 40 ± 12 | 2.0 ± 0.4 |
| (S)-(−)-EPA | 5.0 ± 1.10 | 32 ± 2 | 520 ± 15 | 135 ± 12 | 3.5 ± 1.0 |
| mitomycin | | | | | |

| compd | antitumor activity against P388/ADR, in ip implanted $CDF_1$ mice, treated in ip, qd 1-9 $OD^e$ | $MST^f$, days | % ILS $(surv)^g$ |
|---|---|---|---|
| 1b(AMD) | 0.075 | 12 | 33(0/10) |
| 3b[(±)-EPA] | 0.65 | 40 | 344(4/10) |
| (R)-(+)-EPA | 0.30 | 45 | 400(4/10) |
| (S)-(−)-EPA | 0.80 | 43 | 377(5/10) |
| mitomycin | 1.0 | 45 | 400(5/10) |

$^a\Delta T_m = T_m$ of DNA-drug complex minus $T_m$ of drug-free DNA: concentration of drug 14.0 nM and that of DNA 70 nM in 0.01M phosphate buffer, pH 7.0, 5 × $10^3$ EDTA and 5% $Me_2SO$. Broad $T_m$ of analogues indicate some covalent binding, in contrast to relatively sharp $T_m$ of actinomycin that is indicative of intercalative binding to DNA.
$^b$Binding to purified calf thymus DNA in 20 mM Tris-HCl, ph 7.4 buffer at 37° C.; A values are molar ratios of DNA to drug based on the total amount of drug that is bound both intercalatively and covalently to DNA helix.
$^c$B values are similar ratios assayed on the basis of drugs bound entirely by covalent bonding to DNA base.
$^d$Concentration required for 50% inhibition of growth of actively growing tumor cells in vitro.
$^e$Optimal dose of drugs.
$^f$Median survival time of tumor bearing mice.
$^g$Percent increase in median life time in days of drug-treated dying animals vs those of controls; (survivors), number of 60 days survivors/number of animals tested in the group.

TABLE IV pH-Dependent Ultraviolet Absorption of Synthetic (HPLC Indentified) Deoxyguanosine-EPA Adducts

| site specific adducts (HPLC peak product) | acid (0.1 N HCl) | λ nm max, $neutral^a$ (pH 6.9) | alkaline (0.1) N NaOH |
|---|---|---|---|
| $N^7$-dG | | | |
| (EPA IV-dG) | $257^b$ | 263,285 | 266 |
| | (256,280,sh$^c$) | (263,285) | (266) |
| $O^8$-dG | | | |
| (EPA II-dG) | 247,287 | 247,282 | 250,282 |
| (EPA III-dG) | 243,288 | 252,282 | 247,282 |
| | (242,288) | (247,282) | (248,281) |
| $N^2$dG | | | |
| (EPA I-dG) | 263 | 253 | 257 |
| | (259) | (253) | (257,270 sh) |

$^a$The spectra were recorded with equimolar (R)-(−) and (S)-(+)-DHPA solutions in the blank cuvette; 0.1M $PO_4^{3+}$ buffer.
$^b$Spectra recorded within 5 min after preparation of the acid solution at a low temperature (0° C.); at ≧ 80° C. in 30 min deglyco sylation takes place, which is consistent with $N^7$-dG substitution (mass spectra data).
$^c$Possibly of the anion of the imidazole ring opened ring (see reference below). sh, shoulder. $^d$Data in the parentheses: reported data of the corresponding benzyl analogue substituted dG-adducts.

TABLE V

Inhibition of Nucleic Acid Synthesis, Growth in Vitro and in Vivo of L1210 Murine Leukemia Cells by Actinomycin D and Enantiomers of (+)-EPA

| compd | inhibition of synthesis of nucleic acids in L1210 $IC^a_{50}$ uM $DNA^b$ | $RNA^c$ | inhibition of growth of L1210 cells in culture; $ID^d_{50}nM$ | Activity in mice bearing leukemia L1210 $OD^e$ | % $ILS^f(surv)^g$ |
|---|---|---|---|---|---|
| AMD | 0.38 ± 0.028 | 0.019 ± 0.006 | 60.1 ± 9.8 | 0.025 | 55(0/9) |
| [(±)-EPA] | 0.08 ± 0.019 | 0.024 ± 0.004 | 28.7 ± 8.7 | 0.05 | 186(2/9) |
| (R)-(+)EPA | 0.06 ± 0.015 | 0.031 ± 0.005 | 23.1 ± 7.7 | 0.05 | 199(3/9) |

TABLE V-continued

Inhibition of Nucleic Acid Synthesis, Growth in Vitro and in
Vivo of L1210 Murine Leukemia Cells by Actinomycin D and
Enantiomers of (+)-EPA

| compd | inhibition of synthesis of nucleic acids in L1210 $IC^a{}_{50}$ uM | | inhibition of growth of L1210 cells in culture; $ID^d{}_{50}$nM | Activity in mice bearing leukemia L1210 | |
|---|---|---|---|---|---|
| | $DNA^b$ | $RNA^c$ | | $OD^e$ | % $ILS^f$(surv)$^g$ |
| (S)-(−)EPA | 0.06 ± 0.010 | 0.050 ± 0.005 | 56.8 ± 8.8 | 0.05 | 143(1/9) |

$^a$Drug concentration (micromolor) for 50% reduction of incorporation of [methyl-$^{14}$C]thymidine into DNA$^b$ and [5-$^3$H] uridine into RNA$^c$ from the rate of incorporation of the same radionucleotides in non-drug treated L1210 cells growing actively in vitro.
$^d$Drug concentration (nanomolar) for 50% inhibition of growth relative to growth of non-drug-treated L1210 cells.
$^e$OD, optimal dose of drugs in milligrams/killograms per injection, administered ip on days 1, 5, and 9, following ip inoculation with $10_5$H L1210 cells per CDF$_1$ mouse on day 0.
$^f$% ILS, percent increase in median life span in days, of the tumor-bearing drug-treated dying animals when compared with similar tumor bearing mice but not treated with drugs. (surv), number of over 60 days survivors/number of animals tested.

The analogues are assayed for in vitro growth inhibitory activity against several experimental tumor lines including human and murine leukemia, mouse melanoma, and human lymphoblastic leukemia. Early investigations employing a moderately pure (>66%) R-(+) isomer against CCRF-CEM cell lines gave the first evidence that the R-(+) isomer of EPA is the major active component. Later, with a purer (90%) form of R-(+) and S-(−) isomers, the 50% growth inhibitory dose (ID$_{50}$) for the R-(+) isomer is 2.0 nM compared with a value of 3.5 nM for the S-(−) isomer and 12.5 nM for actinomycin D (data not shown in Tables III and V). Against the murine leukemia L1210, which is less responsive to actinomycin, and also against an actinomycinresistant P388/ADR leukemia, the R-(+) isomer demonstrates about 3 times the potency of AMD in the L1210 line and more than 6-=fold the potency of AMD in the P388/ADR line. The R-(+) isomer is demonstrably superior to actinomycin D in inhibiting the growth of the fast-growing cells; however, this activity in the slower growing B16 mouse melanoma tumor is less pronounced (Tables III and IV).

Inhibition of nucleic acid synthesis in L1210 lymphoid leukemia cells by (±)-EPA and it optical isomers are assayed. AMD is known to be more effective in inhibiting RNA synthesis than DNA synthesis in cells in culture. Table V shows that in L1210 cells the IC$_{50}$ DNA value of AMD is 20 times the IC$_{50}$ RNA value, indicating strong preference shown by AMD for blocking RNA synthesis. In contrast, the racemic (±)-EPA, (R)-(+)-EPA, and (S)-(−)-EPA show about 3 to 1, 2 to 1 and 1 to 1 preference, respectively, for the inhibition of RNA to DNA synthesis. Because of the closeness of the IC$_{50}$ DNA and IC$_{50}$ RNA values for these isomers of EPA (Table V), a modification of the process was introduced in order to account for even a marginal cross-incorporation from the [2-$^{14}$C] uridine into DNA. To achieve this, a digestion of the nucleic acid pellet with DNase-free RNase enzyme, prior to final pelleting of the DNA precipitate is made to ensure that no more than ±8% contamination from [2-$^{14}$C] uridine into DNA takes place, and for this the necessary correction is made in the data reported in Table V.

These inhibitory data demonstrate that (±)-EPA and its enantiomers are more reactive than AMD in inhibiting replication of DNA, probably by virtue of their dual action on DNA, intercalation as well as alkylation. However, the relative efficiency of cell growth inhibitory activity (L1210, ID$_{50}$ values) by these enantiomers do not appear to be directly related to their gross proficiency for DNA or RNA inhibition. Evidently, factors other than only the inhibition of gross DNA and RNA synthesis parameters are more significant for their tumor cell growth inhibitory activity; this action may depend more closely on other subtle effects, namely irreversible inhibition of specific nucleic acid sequences due to site-selective alkylation of dG bases in DNA, which is more than the binding at less sensitive sites.

The analogue (±)-EPA at the optimal dose level demonstrates 2.5 times the percent increase in median life time (% ILS) of P388/S lymphocytic leukemia in CDF$_1$ mice over that effected by AMD. P388/S is highly responsive to the action of AMD. In order to examine a broader spectrum of activity, these optical isomers are tested in two other mouse leukemia cell lines in vivo. One cell line, P388/ADR, is a derivative of the above P388/S made resistant to intercalating agents like actinomycin C. Against this ip implanted tumor in CDF$_1$ mice, on a schedule of treatment by drugs on days 1–9, the % ILS jumped 10-fold, from a value of 33 for actinomycin to a value of 344 for racemic EPA [(±)-3b], with four out of 10 animals treated surviving 60 days, respectively. This remarkable improvement of activity in all the optically active or racemic forms of this analogue is matched by another alkylating agent, mitomycin C, which is known to act in cells via alkylation of DNA. Presumably, the high activities of these agents are derived primarily from their DNA-alkylating property (Table III).

When these agents are tested against another standard leukemia line, L1210 in CDF$_1$ mice, inoculated ip with tumor and treated with ip regimen of drugs administered on days 1, 5, and 9 after tumor inoculation on day 0, the activities of the optical isomers showed measureable differences in terms of % ILS and in the number of long-term survivors (Table V). In addition, the optimum dose levels of all the isomers are equivalent and are about double that of actinomycin, although the potencies of these agents in vitro are found superior to actinomycin.

The enantiomers also demonstrate superior activity to those of AMD in the treatment of two solid tumors in mice, e.g., B$_{16}$ melanoma and C26 colon carcinoma (Table VI). Subcutaneously implanted B16 melanoma in BDF$_1$ mice is a slow growing tumor, but its rate of growth becomes faster when it is implanted ip. Against the ip implanted tumor, ip administered actinomycin is only moderately active; however, against sc implanted tumor, iv administered actinomycin is only marginally active. Compared to AMD, (±)-EPA and its enantiomer show improved activity in both ip and sc implanted tumor in respect of % ILS as well as number of long-term survivors, with the R-(+) enantiomer demonstrating the highest activity (Table VI). In an apparent anomaly, (±)-EPA demonstrates an equiactivity to that of the R-(+) isomer, which is higher than that shown by the S-(−) enantiomer in the ip vs ip treatment (Table VI). This is not consistent with data in other tumors; however, in this connection it should be pointed out that the combined effects of drugs (or enantiomers in this case) can be manifested in several ways, i.e., they can be synergistic, additive, or subtractive.

The C26 colon carcinoma implanted ip in CDF$_1$ mice (Table VI) also respond more favorably to the treatment by EPA enantiomers, with (R)-(+)-EPA, acting as the isomer of choice, demonstrating a higher % ILS and producing a larger number of long-term survivors. However, this superior activity in C26 tumor is less significant, in comparison to the clinically active agent adriamycin which is used as a reference drug, and which is established as the drug of choice against solid tumors in general.

Compared to the previously mentioned faster growing leukemia, the activities of EPA and enantiomers in the solid slower growing tumors are less pronounced. Nonetheless, all the optical isomers of EPA and particularly the R-(+) enantiomer show uniformly superior activity in comparison to the parent drug actinomycin D. AMD is known to be effective primarily against slow growing tumors in humans, e.g., Wilm's tumor in children, choriocarcinoma in pregnant women, and Kaposi's sarcoma in AIDS disease patients. The activities of this alkylating analogue EPA show promise for a superior activity against these tumor lines, with the additional prospect of a broader range of antitumor activity in faster growing leukemias and other tumors that are not responsive to actinomycin.

The following example illustrates the present invention and is not intended to limit the same.

EXAMPLE I

DNA-binding experiments were carried out in 0.01M phosphate buffer (pH7), containing EDTA ($10^{-5}$M). For unwinding studies with covalently closed circular DNA, SV 40 DNA (0.234 ug, BRL, Bethesda, MD) was dissolved in 10 mM Trizma base (pH 7.4) buffer containing 50 mM KCl, 50 mM MgCl$_2$, and 0.1 mM EDTA and incubated with appropriate volumes of drug solution for 60 min at 37° C. After the addition of loading buffer (25% bromophenol blue, 25% xylene cyanol in 30% glycerol), each sample was added to a 1% agarose gel. The gels were run at 35 V overnight using a Tris-borate EDTA buffer (pH 8). The DNA was visualized by staining the gel with ethidium bromide (0.5 ug/mL).

UV Identification of the Deoxyguanosine Adducts. (±)-EPA and enantiomers, 1.7 mM (1 mL) were incubated with deoxyguanosine (17 mM, 1 mL) in 0.5 Tris-HCl buffer (pH 7.4) at 37° C. for 16 h. At the end of incubation, the samples were extracted thoroughly with methylene chloride to remove any unreacted (±)-EPA, (±)-DHPA, or enantiomers. The reaction products were first chromatographed on a Sephadex LH-20 column and eluted with 20% MEOH-H$_2$O (v/v) and 50–80% MeOH-H$_2$O in a linear gradient. After evaporation of the eluates, the residue was separated on a HPLC (Varian 5020) equipped with a C-18, 7.5×250 mm column, particle size 5 μm. A gradient of water-methanol 65–90% at a concave gradient and at a flow rate of 1 mL/min for 150 min was used. Four EPA-dG adducts were isolated corresponding to peaks at retention times 45 min (EPA I-dG), 75 min (EPA II-dG), 85 min (EPA III-dG) and 110 min (EPA IV-dG).

These deoxyguanosine adducts exhibit characteristic substitution-dependent UV spectra in neutral, alkaline, and acid solutions (20° C., pH-1-13); the required pHs of these solutions were adjusted by mixing 50 mM sodium phosphate buffer with NaOH and HCl. Sites of substitution on deoxyguanosine adducts were indicated from the UV peaks which were in close agreement with authentic addicts. (Table IV). Furthermore, one of the adducts, $N^7$-substituted guanosine, which was found unstable in acid pH (0.1N HCl) was incubated for 30 min at 70° C., neutralized to pH 8.0, and extracted to EtOAc. The residue, on evaporation, was subjected to HPLC after increasing the gradient to 90% methanol at 2 mL/min. Two peaks, one minor, 120 min (20%), and the other major, 135 min (75%), were isolated. $N^7$-Deoxyguanosine EPA IV-dG elutes at 95 min in this system. The major peak material from the model analogue was subjected to mass spectrometric analysis; MS, m/z 589 (M-H).

TABLE VI

| Activity of Actinomycin D Analogues on Mice Inoculated with B16 Melanoma or C26 Colon Carcinoma | | | | | | | | | |
|---|---|---|---|---|---|---|---|---|---|
| | | | | B$_{16}$ melanoma[a] | | | | C$_{26}$ colon carcinoma[b] | |
| | | sc-iv | | | ip-ip | | | | |
| compd | OD | MST | % ILS (surv) | OD | MST | % ILS (surv) | OD | MST, days | % ILS (surv) |
| control | 0.9 | 33.0 | | | 19.0 | | | 22.0 | |
| 1b (AMD) | 0.9 | 45.0 | 36(0/9) | 0.25 | 29.0 | 52(0/9) | 0.30 | 33.5 | 52(0/10) |
| 3b[(±)-EPA] | 1.0 | 54.0 | 64(0/9) | 0.30 | 39.0 | 105(2/9) | 0.60 | 36.0 | 64(0/10) |
| (R)-(+)-EPA | 1.0 | 56.0 | 70(1/9) | 0.30 | 39.0 | 105(2/9) | 0.60 | 41.5 | 89(2/10) |
| (S)-(−)-EPA | 1.0 | 53.0 | 60(1/9) | 0.30 | 33.0 | 74(2/9) | 0.90 | 36.0 | 64(1/10) |
| adriamycin | 5.0 | 59.0 | 79(1/9) | 5.0 | 60.0 | 224(7/9) | 2.50 | 48.0 | 118(3/10) |

0.2 ml of brei (tumor weight/Hank's balanced salt solution, (1:5) of B16 implanted sc or ip into groups of nine BDF$_1$ mice on day 0. Drugs administered iv on day 1 or ip on days 1, 5, and 9, following tumor implantation. Primary colon C26 carcinoma (tripan blue excluding, 2.5 × 10$^5$ cells/mouse) implanted in CDF$_1$ mice on day 0; drug administered ip on days 1, 5, and 9. OD, optimal dose in milligrams/milliliter of vehicle, and administered iv or ip in 0.1 mL of
vehicle (5% v/v Me$_2$SO-saline). MST, median survival times in days of tumor bearing and non-drug treated (control) or drug-treated mice. % ILS, percent increase in life span of drug treated groups over the control group of test animals, excluding survivors. (surv), number of sixty day survivors/number of mice treated with drug.

I claim:

1. The R-(+) enantiomeric form of ± racemic-(2,3-epoxypropoxy) actinomycin D having the formula:

13
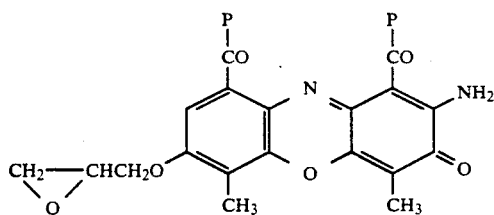
wherein the P's are:
Thr—D—Val—Pro—Sar—MeVal
└──────O──────┘
\* \* \* \* \*
14
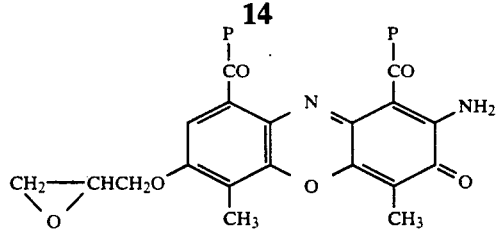
wherein the P's are:
Thr—D—Val—Pro—Sar—MeVal
└──────O──────┘
\* \* \* \* \*